United States Patent [19]

Brown et al.

[11] Patent Number: 5,074,872
[45] Date of Patent: Dec. 24, 1991

[54] LANCET ASSEMBLY

[75] Inventors: Michael K. Brown; Mohammed Kheiri, both of Elkhart, Ind.; D. Glenn Purcell, Edwardsburg, Mich.; William Taylor, Goshen; Robert Whitson, Osceola, both of Ind.

[73] Assignee: Miles Inc., Elkhart, Ind.

[21] Appl. No.: 557,452

[22] Filed: Jul. 25, 1990

Related U.S. Application Data

[62] Division of Ser. No. 367,862, Jun. 19, 1989, Pat. No. 4,990,154.

[51] Int. Cl.$^5$ ............................................. A61B 17/32
[52] U.S. Cl. .................................... 606/182; 606/167
[58] Field of Search ............... 606/181, 167, 170, 172, 606/182, 183, 184

[56] References Cited

U.S. PATENT DOCUMENTS

| | | | |
|---|---|---|---|
| 3,060,937 | 10/1962 | Griffitts | 606/181 |
| 4,375,815 | 3/1983 | Burns | 606/182 |
| 4,388,925 | 6/1983 | Burns | 606/182 |
| 4,445,510 | 5/1984 | Rigby | 606/182 |
| 4,462,405 | 7/1984 | Ehrlich | 606/182 |
| 4,517,978 | 5/1985 | Levin | 606/182 |
| 4,527,561 | 7/1985 | Burns | 606/182 |
| 4,577,630 | 3/1986 | Nitzsche | 606/182 |
| 4,653,513 | 3/1987 | Dombrowski | 606/182 |
| 4,869,249 | 9/1989 | Crossman | 606/182 |
| 4,895,147 | 1/1990 | Bodicky | 606/182 |
| 4,976,724 | 12/1990 | Nieto | 606/181 |

Primary Examiner—Robert A. Hafer
Assistant Examiner—Michael Brown
Attorney, Agent, or Firm—Roger N. Coe

[57] ABSTRACT

A lancet assembly includes a reusable base unit that defines a handle for a lancet assembly and houses a biasing mechanism for driving a lancet into the finger of a user. The base unit includes a spring biased hammer that once cocked, can be released to drive a lancet. A lancet is included in a disposable end cap that may be releasably attached to one end of the base unit. The end cap includes integral resilience spring fingers that maintain the lancet completely within the end cap before and after use, and functions to return the lancet after engagement of the lancet and hammer. The end cap can be rotated to orient the end cap relative to user's finger to control the depth of penetration of the lancet into the user's finger.

2 Claims, 1 Drawing Sheet

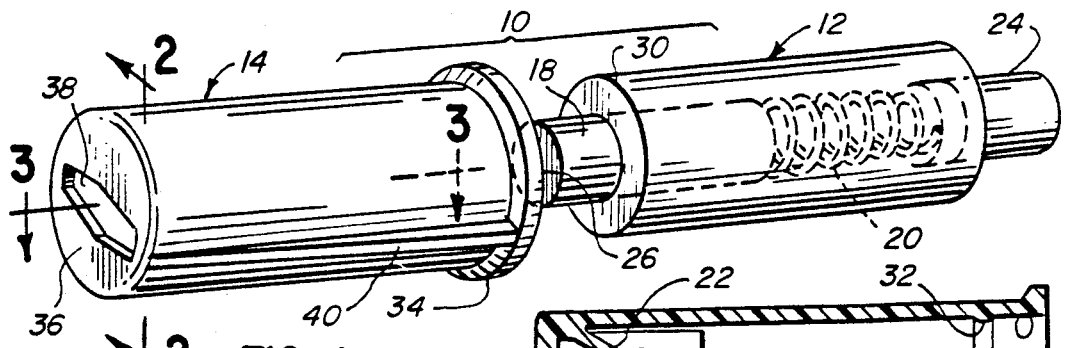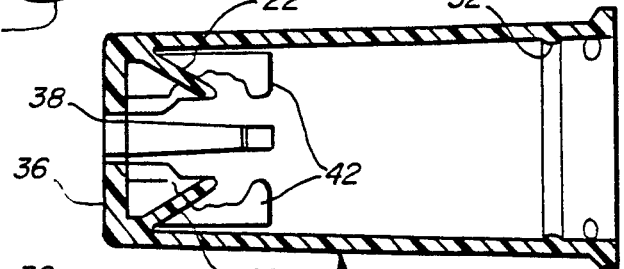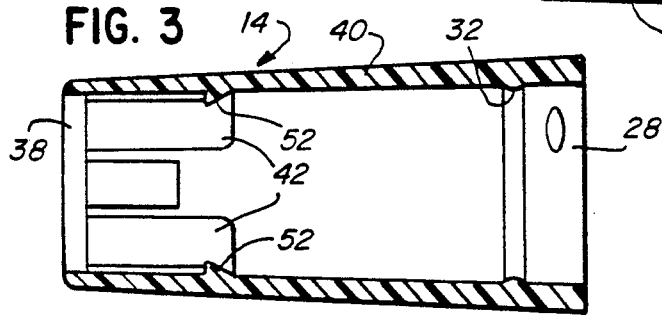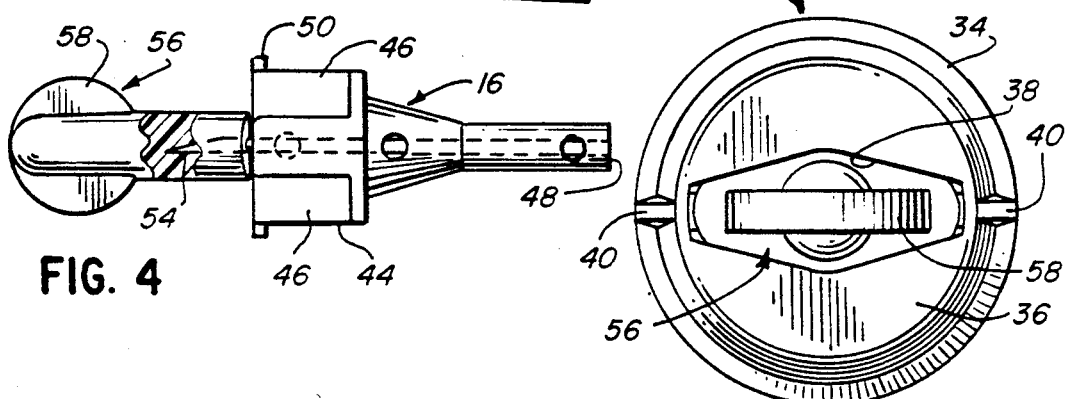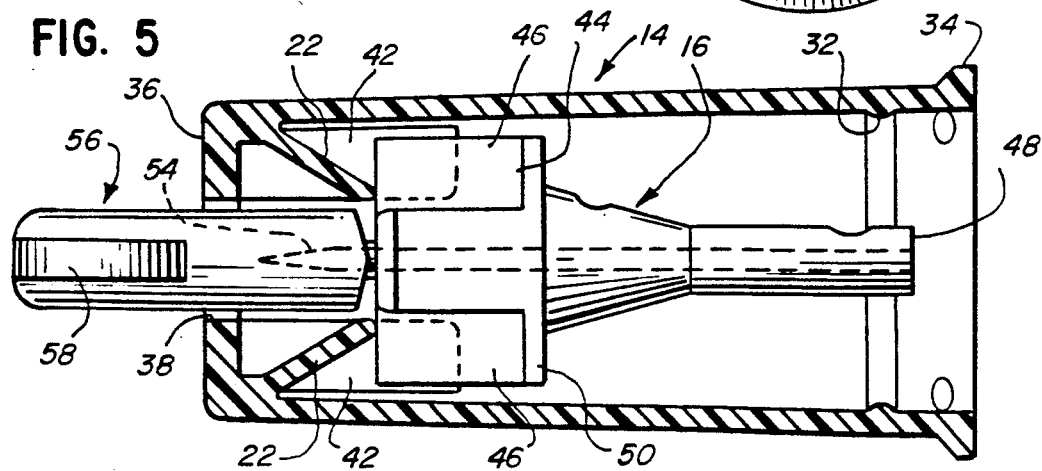

LANCET ASSEMBLY

This is a division of application Ser. No. 367,862, filed on June 19, 1989, now U.S. Pat. No. 4,990,154.

BACKGROUND OF THE INVENTION

A. Field of the Invention.

The device of the present invention generally relates to a new and improved lancet assembly for puncturing the skin of a user to obtain a blood sample; and, more particularly, to a new and improved lancet assembly including a disposable end cap containing a one piece lancet.

B. Description of the Prior Art

Sharp pointed lancets are employed to make a puncture or penetration of a patient's skin in order to provide a small outflow of blood. Various tests may be employed with only small amounts of blood so that blood flowing from a finger prick is normally sufficient for these tests. Tests on the blood sample often include contacting a paper strip or reagent pad on a strip carrying chemistry with blood from the wound or puncture.

Lancet assemblies now available include a driving member that grips a lancet. Loading and removing a lancet from the driving member of the assembly requires extra care by the user to avoid being punctured. The lancet must be carefully gripped to avoid contact with the sharp end of the lancet. Present day concerns about communicable diseases transmitted through body fluids such as blood increases the risks of handling these lancets.

Current devices require the user to remove a protective cover from the sharp end of a lancet, and load the exposed lancet into a lancet assembly. After use of the assembly, the point of the lancet is exposed. Users of these devices, such as nurses, are repeatedly handling these used, exposed lancets and have a high risk of puncture by a used lancet and resultant exposure to contamination through the blood on the lancet.

Some designs of lancets include a end cap with the sharp end of the lancet contained within the end cap after use, and the opposite end of the lancet sticking out of the end cap. Upon removal of the end cap after use, it is possible for the user to be stuck with an infected lancet simply by pressing on the exposed end of the lancet thereby moving the sharp end of the lancet out of the end cap. This risk is especially high for professional users such as nurses who place used lancets in their pockets. At the end of the day the nurses reach into their pockets and pull out used items including lancets. Upon reaching into his or her pocket, the nurse can press the back end of a lancet thereby exposing the contaminated sharp point.

One example of a known lancet is illustrated in U.S. Pat. No. 3,030,959. The lancet of this patent includes a spindle designed for housing a replaceable magazine containing a stock of needles. A feeding device for feeding a needle to be used is also disclosed. After a needle is used, it is maintained in the lancet until another needle from the magazine is loaded. As the new needle is advanced, the needle preceding it is ejected from the lancet. The lancet assembly of U.S. Pat. No. 3,030,959 ejects an unprotected, exposed and contaminated needle which increases the risk of puncture by the user of the lancet assembly.

A disposable needle probe package is disclosed in U.S. Pat. No. 4,637,403. The needle package is frictionally held in the medical testing system by snapping, threading or similar procedures, and it is releasable by pushing the probe package out of the medical monitoring system. Once the probe package is released from the monitoring system, however, the needle is exposed and handling can result in puncturing the skin of the user thereby exposing the user to contaminated blood.

A lancet assembly intended to be disposable with no part of the assembly reused is disclosed in U.S. Pat. No. 4,375,815. Examples of other lancet assemblies intended to be totally disposable, as opposed to disposing only the lancet, are disclosed in U.S. Pat. Nos. 4,388,925; 4,553,541; 4,449,529 and 4,535,769.

A disposable lancet defined by a plunger is disclosed in U.S. Pat. Nos. 4,712,548 and 4,738,261. After this device has been used, the lancet is exposed with the risk that someone handling the used device could be punctured by the contaminated lancet.

Lancet assemblies in which used, exposed lancets must be removed with the risk of puncture are disclosed in U.S. Pat. Nos. 4,416,279; 4,462,405; 4,442,836 and 4,469,110.

U.S. Pat. No. 4,545,376 discloses a one piece, plastic lancet consisting of a handle and a tip. Once a protective yoke is removed, the lancet tip is completely exposed and can accidentally puncture a user.

Lancet assemblies that are totally disposable with no reusable components are disclosed in U. S. Pat. Nos. 4,624,253; 4,616,649 and 4,539,988.

A lancet assembly with a lancet exposed after use is disclosed in U.S. Pat. No. 4,452,243.

Some lancet assemblies provide for the depth of penetration of the lancet into the skin of a user or patient to be adjustable. Adjustability has been accomplished in some prior art lancet assemblies by using removable end caps. Typically, prior art lancet assemblies can be used with one of two end caps each having different size holes allowing different amounts of the skin of the finger to be contacted. With a greater amount of skin fitting into the hole, the lancet can pierce deeper into the skin of the finger. With a lesser amount of skin fitting into the end cap through the hole, a shallower piercing will occur.

There is a need for a lancet assembly in which the lancet is completely contained within a portion of the lancet assembly both before and after use such that the user can dispose of the lancet without risk of puncture. There also is a need for a lancet assembly that is easily and quickly adjustable to control the depth of penetration of the lancet into the finger of a user or patient. In addition, there is a need for a lancet which is as painless as possible.

SUMMARY OF THE INVENTION

An object of the present invention is to provide a new and improved lancet assembly for piercing the skin of a user to extract blood for testing purposes.

Another object of the present invention is to provide a new and improvement lancet assembly that can be easily adjusted to control the depth of penetration into the skin of the user.

A further object of the present invention is to provide a new and improved lancet assembly that includes a disposable, easily detachable end cap in which is totally contained a lancet that is not exposed before or after use.

A still further object of the present invention is to provide a new and improved lancet assembly that includes a molded, one piece lancet that can be fixedly secured in an end cap, separate from a driving member of the lancet assembly.

A yet further object of the present invention is to provide a new and improved lancet assembly for piercing the skin of a user as painlessly as possible in order to obtain blood for diagnostic test purposes.

Briefly, the present invention is directed to a new and improved device commonly referred to as a lancet assembly used for puncturing the skin of a user or patient to allow blood from the puncture to be tested. The lancet assembly includes a base unit that defines a handle and houses a spring driven hammer. The hammer extends outward from one end of the base unit and is cocked by merely pushing the hammer into the base unit. This action compresses a spring and latches the hammer within the base unit.

The lancet assembly also includes a disposable end cap that can be detachably secured to the base unit. The end cap includes an elongated slot through which a lancet extends when struck by the hammer. By rotating the end cap relative to the base unit, the slot is rotated relative to the finger of a user or a patient. In a first position of the end cap the lancet will penetrate deep into the skin of the user or patient. In a second position of the end cap the lancet will penetrate a shallower depth into the skin of the patient or user.

The end cap includes integral resilient spring fingers formed on the inside of the end cap. A molded on piece lancet is positioned within the end cap against the spring fingers. When the end cap is attached to the base unit and the hammer released, the hammer strikes the lancet driving it through the slot in the end of the end cap. The resilient spring fingers then act to return the lancet to a position totally within the end cap.

The lancet of the present invention includes a collar member with indexing structure. The indexing structure interfaces with complimentary structure on the inner peripheral surface of the end cap to lock the lancet relative to the end cap such that the lancet will move with the end cap when the end cap is rotated to orientate the elongated slot. The lancet also includes a piercing end that is driven into the skin of the user or patient, and an anvil end that is struck by the hammer. After the lancet has been used, the end cap can be easily removed or snapped off of the base unit and no portion of the lancet is exposed outside of the end cap. In this condition, the end cap can be carried or handled without risk of puncturing the hand of the user and exposing the user to contaminated blood.

BRIEF DESCRIPTION OF THE DRAWINGS

The above and other objects and advantages and novel features of the present invention will become apparent upon reading the following detailed description of a preferred embodiment of the invention illustrated in the accompanying drawings wherein:

FIG. 1 is an exploded, enlarged, perspective view of a lancet assembly constructed in accordance with the objectives of the present invention;

FIG. 2 is a vertical cross sectional view of the end cap of the lancet assembly taken along line 2-2 in FIG. 1;

FIG. 3 is a vertical cross sectional view of the end cap taken along line 3—3 in FIG. 1;

FIG. 4 is an enlarged, partially cross sectioned view of a lancet used in the lancet assembly illustrated in FIG. 1;

FIG. 5 is an enlarged view similar to FIG. 2 with a lancet mounted within the end cap; and FIG. 6 is an end view of the end cap with a lancet mounted therein.

While the invention is susceptible to various modifications and alternative forms, specific embodiments thereof have been shown by way of example in the drawings and will be described in detail herein. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Referring initially to the drawings and specifically to FIG. 1; there is illustrated a lancet assembly generally designated by the reference numeral 10. The lancet assembly 10 prevents accidental puncturing of the skin of a professional user of the assembly 10 such as a nurse or other health care professional. The lancet assembly 10 includes two separate components, a reusable base unit generally designated by the reference numeral 12, and disposable end cap generally designated by the reference numeral 14. The combination of a reusable base unit 12 with a disposable end cap 14 significantly reduces the cost of the lancet assembly 10 and increases the safety to the user.

The end cap 14 is designed to house a lancet generally designated by the reference numeral 16. The base unit 12 houses a hammer 18 that engages or strikes the lancet 16 and drives the lancet 16 into the skin of a patient or user. The hammer 18 differs from the typical driving member in prior art lancet assemblies. The hammer 18 functions as a striking element, striking the lancet 16 as opposed to gripping the lancet and carrying the lancet with the hammer. Instead of a gripping structure, the hammer 18 includes a flat striking face 26. By using a hammer 18 instead of a driving member that grips the lancet 16, the lancet 16 does not need to extend out of the end cap 14 to be attached to the hammer 18. Rather, the lancet 16 is located totally within the end cap 14. This increases the safety of the lancet assembly 10 since once the lancet 16 has been used and it is contaminated with blood or other body fluids, the end cap 14 can be disposed of without the danger of the contaminated lancet 16 contacting the finger of the user.

The hammer 18 should be of considerably more mass than the lancet 16. Due to the greater mass, as the hammer 18 is accelerated towards the lancet 16 under the influence of a compressed spring 20 in the base unit 12, the transference of linear momentum from the impact of the hammer 18 gives the lancet 16 a high velocity in a direction outward of the end cap 14. The lancet 16 is then returned to a position completely within the end cap 14 by spring fingers 22, molded on the inside of the end cap 14.

The base unit 12 is similar to prior art lancet assemblies. By pushing the hammer 18 inwardly into the base unit 12, the spring 20 is compressed and stores energy. As the hammer 18 is moved into the base unit 12, the hammer 18 is latched in position and held within the base unit 12 until a button 24 is pushed by a user. Pushing the button 24 releases the hammer 18. The hammer 18 is then driven outwardly of the base unit 12 under the biasing force of the spring 20.

The disposable end cap 14 includes an open end 28 which snaps over a hammer end 30 of the base unit 12. A snap or friction fit is provided by an inner peripheral rim 32 on the end cap 14. The engagement of the rim 32 with the outer peripheral surface of the base unit 12 holds the end cap 14 onto the base unit 12 with the hammer 18 aligned to extend into the open end 28 of the disposable end cap 14. To allow easy removal of the end cap 14 for disposal, a flange 34 is formed on the outer periphery of the disposable end cap 14 adjacent the open end 28. After blood has been drawn, the user of the lancet assembly 10 may remove the disposable end cap 14 merely by pushing against the flange 34 to move the end cap 14 off the end 30 of the base unit 12.

The disposable end cap 14 includes a closed end 36 with an elongated slot 38 formed in the closed end 36. The slot 38 is of a length that is greater than its width. This slot 38 controls the depth of penetration of the lancet 16 into the skin of a patient. More specifically, by aligning the length of the slot 38 with the length of a patent's finger, more of the patient's skin is moved into the slot 38 allowing deeper penetration of the lancet 16 into the patient's finger. By rotating the end cap 14 such that the length of the slot 38 extends across the finger of the patient, less skin enters into the slot 38 and shallower penetration of the lancet 16 into the skin results. Consequently, the user of the lancet assembly 10 can control the depth of penetration of the lancet 16 into the skin of a patient by rotating the disposable end cap 14 relative to the base unit 12.

The user of the lancet assembly 10 can ascertain the orientation of the slot 38 by viewing the location of a pair of ribs 40 formed on opposite sides of the disposable end cap 14. The ribs 40 are aligned with the ends of the longitudinal slot 38. By determining the location of the ribs 40 relative to the finger of a patient, a user can determine whether the lancet assembly 10 is aligned for deep or shallow penetration.

The end cap 14 is designed to contain the lancet 16 entirely within it before and after use of a lancet assembly 10. The lancet 16 is maintained within the end cap 14 before use and returned to a position within the end cap 14 after use by the resilient spring fingers 22 integrally molded on the inside of the end cap 14. Preferably, the end cap 14 is molded of polyethylene which is a flexible material allowing the spring fingers 22 to be molded as a single piece with the end cap 14. Polyethylene provides sufficient resilience to return the lancet 16 to a position within the end cap after the lancet 16 has been struck by the hammer 18.

The movement of the lancet 16 is guided by ribs 42 molded on the interior of the end cap 14. The ribs 42 also function to index a fluted collar 44 on the lancet 16. The fluted collar 44 includes arms or flutes 46 that function as indexing structures by engaging the ribs 42 of the end cap 14. This engagement of the ribs 42 and arms 46 aligns the lancet 16 within the end cap 14. The lancet 16 includes an anvil end 48 that is engaged by the hammer 18 to drive the lancet 16 through the slot 38 of the end cap 14. As this occurs, the ribs 42 engage the arms 46 guiding the movement of the lancet 16 as driven by the hammer 18 and as returned to its original position by the spring fingers 22. In addition, the engagement of the indexing structure as defined by the ribs 42 and arms 46 allows the lancet 16 to rotate with the end cap 14 as the end cap 14 is rotated relative to the base unit 12 to align the slot 38 with the length or width of a finger of a patient.

In one embodiment of the present invention, a user purchases the base unit 12 and can use the base unit many times before replacement is necessary. The disposable end caps 14 are purchased in quantity. The end caps 14 include the lancet 16 already assembled within the end cap 14. The lancet 16 is located within the end cap 14 with the arms 46 engaging the ribs 42. A flange 50 on the fluted collar 44 is snapped behind snaps 52 (FIG. 3) formed on the inner peripheral surface of the end cap 14. The snaps 52 hold the lancet 16 within the end cap 14 and prevent it from falling out the open end 28 prior to attaching the end cap 14 to the base unit 12.

The lancet 16 includes a needle or other sharp object 54 that pierces the skin of a patient. Prior to actual use, the needle 54 is covered by a needle plug 56. The needle plug 56 is made of a soft material into which the needle 54 extends. The needle plug 56 includes a flat griping surface 58 that extends through the slot 38 when the lancet 16 is mounted or assembled within the end cap 14. To use the lancet assembly 10, a user snaps a disposable end cap 14 onto the base unit 12. The user then grips the gripping surface 58 of the needle plug 56, and with slight pulling pressure removes the needle plug 56 from the needle 54. The spring fingers 22 then move the lancet 16 inside the end cap 14 such that the needle 54 is safely within the end cap 14. The lancet 16 is also held into position within the end cap 14 by the snaps 52 such that the anvil end 48 of the lancet 16 does not extend through the open end 28 of the end cap 14. Thus, while the end cap 14 is attached to the base unit 12, no portion of the lancet 16 is exposed outside the end cap 14.

Once the end cap 14 has been snapped onto the base unit 12 and the needle plug 56 removed from the needle 54, the user may push the button 24 to release the hammer 18 under the influence of the spring 20. The hammer 18 strikes the anvil end 48 of the lancet 16 driving the lancet 16 against the spring fingers 22. The needle 54 moves through the slot 38 and into the skin of a patient. Once the momentum of the hammer 18 has been exhausted, the spring fingers 22 quickly return the needle 54 to the position illustrated in FIG. 5. In this position, the needle 54 is completely within the end cap 14. After a sample of blood has been drawn, the user may snap off the disposable end cap 14 merely by engaging the flange 34 with a thumb and popping or snapping the end cap 14 off the base unit 12. The spring fingers 22 and the snaps 52 hold the lancet 16 entirely within the end cap 14. Since the hammer 18 strikes the lancet 16 rather than gripping it, the anvil end 48 of the lancet 16 does not extend outside of the end cap 14. The contaminated disposable end cap 14 can then be handled by the user without the danger of engaging the contaminated needle 54, or hitting the anvil end 48 and pushing the needle 54 outside the end cap 14 where it can puncture the skin of the person handling the end cap 14.

Another advantage of the spring fingers 22 is that they cause the needle 54 to be quickly retracted from the skin of a patient and this results in less pain for the patient.

The lancet assembly 10 of the present invention provides increased safety for the user by totally containing the contaminated lancet 16 within the end cap 14. After the lancet 16 has been used and the end cap 14 removed from the base unit 14, there is no portion of the lancet 16 outside the end cap 14 that can be engaged by the user during handling. Consequently, the contaminated needle 54 cannot be contacted by the user and disposal of the end cap 14 can be accomplished safely.

What is claimed and sought in United States Letters Patent is:

1. A lancet for a lancet assembly for piercing skin of a user upon engagement by a hammer housed in said lancet assembly, said lancet comprising:

a first, skin piercing end for piercing the skin of a user of the lancet assembly upon said lancet being driven by a hammer in said lancet assembly, a second, anvil end adapted for engagement by said hammer, and a collar intermediate said first, skin piercing end and said second, anvil end, said collar including orienting structure for orienting said lancet in said lancet assembly and for preventing rotation of said lancet relative to said lancet assembly.

2. The lancet set forth in claim 1 further comprising a flange on said collar for engaging said lancet assembly to limit the travel of said lancet in said lancet assembly upon engagement by said hammer.

* * * * *